(12) United States Patent
Linhart et al.

(10) Patent No.: US 7,862,828 B2
(45) Date of Patent: Jan. 4, 2011

(54) ALLERGY VACCINES CONTAINING HYBRID POLYPEPTIDES

(75) Inventors: Birgit Linhart, Weißenkirchen (AT); Dietrich Kraft, Vienna (AT); Rudolf Valenta, Theresienfeld (AT)

(73) Assignee: Biomay AG, Vienna (AT)

( * ) Notice: Subject to any disclaimer, the term of this patent is extended or adjusted under 35 U.S.C. 154(b) by 104 days.

(21) Appl. No.: 10/026,914

(22) Filed: Dec. 27, 2001

(65) Prior Publication Data

US 2002/0173625 A1 Nov. 21, 2002

(30) Foreign Application Priority Data

Dec. 28, 2000 (EP) .................................. 00128660

(51) Int. Cl.
| | |
|---|---|
| A61K 39/00 | (2006.01) |
| A61K 39/36 | (2006.01) |
| A61K 39/38 | (2006.01) |
| A61K 45/00 | (2006.01) |
| A61K 47/00 | (2006.01) |
| A61K 51/00 | (2006.01) |

(52) U.S. Cl. .................. 424/275.1; 424/1.69; 424/9.81; 424/178.1; 424/184.1; 424/185.1; 424/192.1; 424/278.1; 435/4; 435/41; 435/69.7; 436/513

(58) Field of Classification Search ............... 424/185.1, 424/193.1, 275.1, 171.1, 184.1, 9.81, 134.1, 424/139.1, 156.1, 192.1; 530/350, 395, 806–858, 530/379; 435/41, 69.1, 69.3, 69.7, 70.1, 435/70.2, 71.1, 243, 410; 436/513

See application file for complete search history.

(56) References Cited

U.S. PATENT DOCUMENTS

| | | | | |
|---|---|---|---|---|
| 5,804,201 A | * | 9/1998 | King ....................... | 424/275.1 |
| 5,958,415 A | * | 9/1999 | Yuuki et al. ............... | 424/185.1 |
| 5,968,526 A | * | 10/1999 | Garman et al. ........... | 424/275.1 |
| 6,008,340 A | * | 12/1999 | Ball et al. .................. | 536/23.6 |

FOREIGN PATENT DOCUMENTS

| | | |
|---|---|---|
| WO | WO 93/08280 | 10/1992 |
| WO | WO 95/34578 | * 12/1995 |
| WO | WO 97/06263 | 8/1996 |
| WO | WO 97/07218 | * 2/1997 |

OTHER PUBLICATIONS

Vrtala et al. 1997. J. Cin. Invest. 99(7): 1673-1681.*
Vrtala et al. 1996. J. All. Clin. Immun. 97:781-787.*
Vrtala et al., (1996. J. Allergy Clin Immun. vol. 97(3):781-787).*
Pauli, G., et al., "Comparison of genetically engineered hypoallergenic rBet v 1 derivatives with rBet v 1 wild-type by skin prick and intradermal testing: results obtained in a French population," *Clinical and Experimental Allergy*, 30: 1076-84 (2000).

(Continued)

*Primary Examiner*—Mark Navarro
*Assistant Examiner*—JaNa Hines
(74) *Attorney, Agent, or Firm*—Dobe Law Group, LLC; Christopher Aniedobe

(57) ABSTRACT

Hybrid polypeptides comprising at least two different allergenic proteins or fragments thereof wherein each fragment consists of at least eight consecutive amino acids of the respective allergenic protein are disclosed. The hybrid polypeptides and polynucleotides coding therefor can be used as pharmaceutical compositions, in particular as vaccines.

7 Claims, 6 Drawing Sheets

Figure 3:
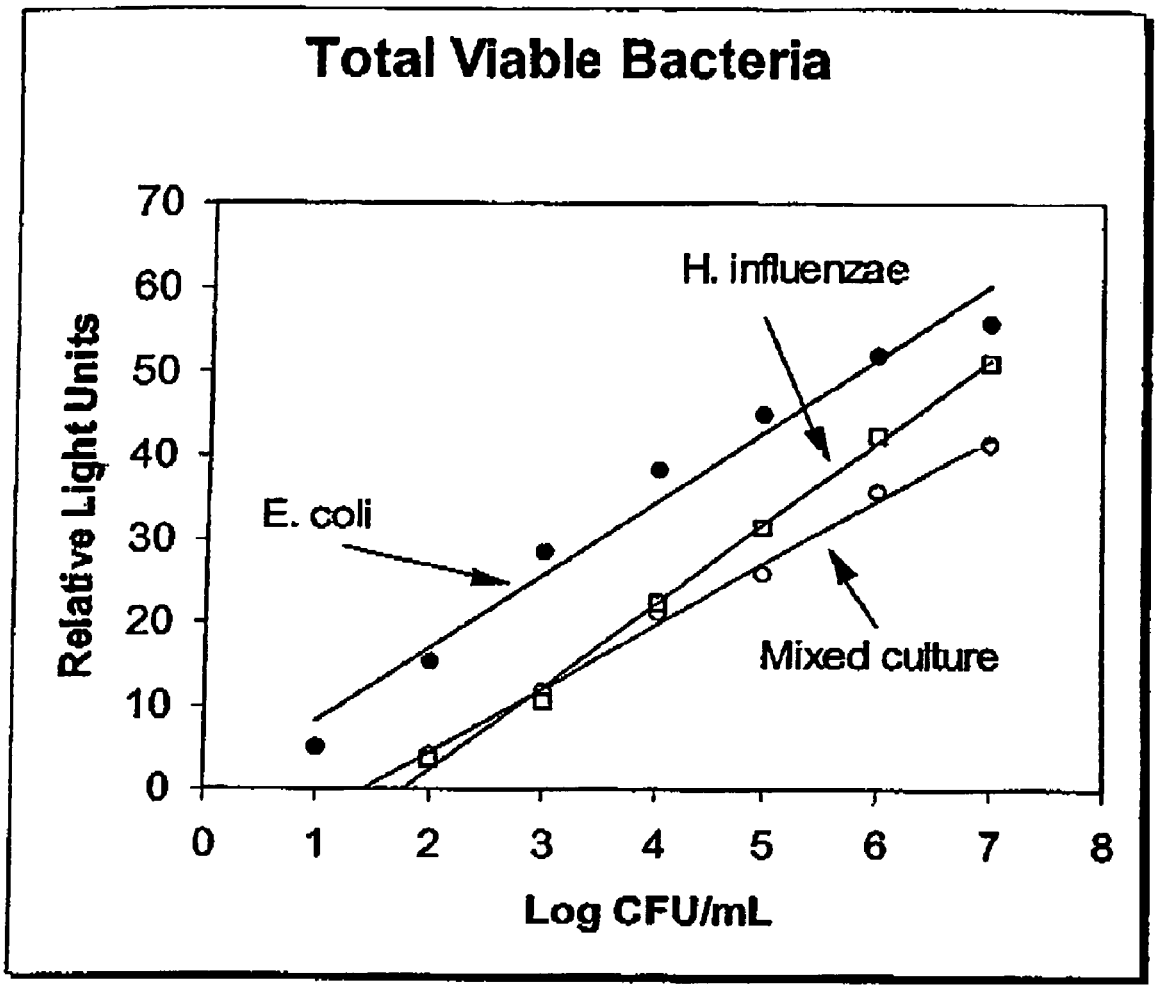

| GENUS | % of TOTAL |
|---|---|
| Bacillus | 12 |
| Cedecea | <1 |
| Citrobacter | 19 |
| Enterobacter | 5 |
| Eschericia | 23 |
| Klebsiella | 2 |
| Kluyvera | 23 |
| Pseudomonas | 1 |
| Providencia | 3 |
| Salmonella | 5 |
| Serratia | 7 |
| Staphylococcus | <1 |

OTHER PUBLICATIONS

Van Hage-Hamsten, M., et al., "Skin test evaluation of genetically engineered hypoallergenic derivatives of the major birch pollen allergen, Bet v 1: Results obtained with a mix of two recombinant Bet v 1 fragments and recombinant Bet v 1 trimer in a Swedish population before the birch pollen season," *The Journal of Allergy and Clinical Immunology*, 104: 969-77 (Nov. 1999).

Vrtala, S., et al., "Conversion of the Major Birch Pollen Allergen, Bet v 1, into Two Nonanaphylactic T Cell Epitope-containing Fragments," *J. Clin. Invest.*, 99:1673-1681 (Apr. 1997).

Vrtala, S., et al., "Immunologic characterization of purified recombinant timothy grass pollen (*Phleum pratense*) allergens (Phl p 1, Phl p 2, Phl p 5)," *The Journal of Allergy and Clinical Immunology*, 97: 781-87 (Mar. 1996).

Vrtala, S., et al., "Molecular, Immunological, and Structural Characterization of Phl p 6, a Major Allergen and P-Particle-Associated Protein from Timothy Grass (*Phleum pratense*) Pollen," *The Journal of Immunology*, 163: 5489-96. (1999).

Mellerup, M.T., et al., "Safety of allergen-specific immunotherapy. Relation between dosage regimen, allergen extract, disease and systemic side-effects during induction treatment," *Clinical and Experimental Allergy*, 30: 1423-1429 (2000).

Noon, L., et al., Prophylactic Inoculation Against Hay Fever, *The Lancet*, 1572-1573 (Jun. 10, 1911).

Niederberger, V., et al., "IgE antibodies to recombinant pollen allergens (Phl p 1, Phl p 2, Phl p 5, and Bet v 2) account for a high percentage of grass pollen-specific IgE," *The Journal of Allergy and Clinical Immunology*, 101: 258-64 (Feb. 1998).

Bousquet, J., et al., "Allergen immunotherapy: therapeutic vaccines for allergic diseases," *The Journal of Allergy and Clinical Immunology*, 102: 558-62 (Oct. 1998).

Durham, S.R., et al., "Immunologic changes associated with allergen immunotherapy," *The Journal of Allergy and Clinical Immunology*, 102: 157-64 (Aug. 1998).

Laffer, S., et al., "Comparison of recombinant timothy grass pollen allergens with natural extract for diagnosis of grass pollen allergy in different populations," *The Journal of Allergy and Clinical Immunology*, 98: 652-58 (Sep. 1996).

European Search Report, EP 01 13 0292.

B. Pandjaitan et al.; pET-Prof, A Plasmid for High-Level Expression of Recombinant Peptides Fused to a Birch Profilin-Derived Hexadecapeptide Tag: A System for the Detection and Presentation of Recombinant Antigens, *Gene*, 237(2): 333-342 (1999).

L. Zhang et al.; "Antigen- and Isotype-Specific Immune Responses to a Recombinant Antigen-Allergen Chimeric (RAAC) Protein"; *Journal of Immunology*, 151(2): 791-799 (1993).

B. Linhart et al.; "Genetically Engineered Hybrid Vaccines for the Treatment of Grass Pollen Allergy", *Journal of Allergy and Clinical Immunology*, 107(2): S56 (2001-02).

F. Kussebi et al.; "A Novel Type of a Vaccine for Bee Venom Allergy Obtained by Gene Fusion of the Two Major Allergens", *Allergy*, 56 (S68): 13 (2001).

* cited by examiner

FIGURE 1

| GENUS | % of TOTAL |
|---|---|
| Bacillus | 12 |
| Cedecea | <1 |
| Citrobacter | 19 |
| Enterobacter | 5 |
| Eschericia | 23 |
| Klebsiella | 2 |
| Kluyvera | 23 |
| Pseudomonas | 1 |
| Providencia | 3 |
| Salmonella | 5 |
| Serratia | 7 |
| Staphylococcus | <1 |

FIGURE 2

| Total Viable Cells, cfu/ml | Observed Relative Light Units | Calculated *E. coli*, cfu/ml | *E. coli* % of Total |
|---|---|---|---|
| 100,000 | 24.8 | 22,364 | 22 |
| 10,000 | 18.7 | 2,421 | 24 |
| 1,000 | 13.5 | 223 | 22 |

ALLERGY VACCINES CONTAINING HYBRID POLYPEPTIDES

Type I allergy is a genetically determined hypersensitivity disease affecting almost 500 million individuals worldwide. Immediate symptoms (allergic rhinoconjunctivitis, asthma, anaphylactic shock) as well as late symptoms (atopic dermatitis, certain forms of allergic asthma bronchiale) are based on the recognition of allergens by IgE antibodies. Immediate symptoms result from the allergen-induced crosslinking of effector cell-bound IgE and the subsequent release of biological mediators (e.g., histamine, leukotrienes) whereas late symptoms can be caused by IgE-mediated presentation of allergens to T cells and eosinophil activation.

The only curative therapy approach, allergen-specific immunotherapy, is based on the systemic administration of allergens to patients in order to induce allergen-specific "unresponsiveness" (Noon, Lancet 1911, 1: 1572-1573; Bousquet et al. (1998) J Allergy Clin Immunol 102: 558-562; Durham and Till (1998) J. Allergy Clin. Immunol. 102, 157-164). Using conventional technologies it has not been possible to produce pure allergens for specific immunotherapy and hence, vaccination is performed with allergen extracts. These extracts consist of allergens and non-allergenic components which are difficult to standardize. Therefore patients cannot be treated according to their specific sensitization profile and anaphylactic side effects, due to the administration of allergenic material are frequently observed (Mellerup et al. (2000). Clin. Exp. Allergy 30, 1423-1429).

It is an objective of the present invention to provide an advantageous composition for the treatment or prevention of allergic disorders.

Surprisingly the inventors found that it is possible to generate hybrid allergens assembling the epitopes of immunologically distinct allergens for diagnosis and therapy of Type I allergy. The invention therefore relates to a hybrid polypeptide comprising at least two different allergenic proteins or fragments thereof wherein each fragment consists of at least eight consecutive amino acids of the respective allergenic protein.

In the broadest scope of the present invention any polypeptide may be used in the hybrid polypeptide which may be involved in vaccination. The polypeptide may be derived from viruses such as HI, HC-viruses, bacteria, tumor antigens or plant allergens.

The allergenic proteins from which the hybrid polypeptide is derived may preferably be a plant allergen. The different allergenic proteins may be derived from a common source such as the pollens of a certain plant species. Several different allergenic proteins contained in the allergen source may be identified and used for the preparation of the hybrid polypeptide of the invention. The present invention, however, encompasses also a hybrid polypeptide comprising sequences derived from allergenic proteins from different sources. The term "allergenic proteins or fragments thereof" comprises also modifications of the allergens wherein the sequence of the naturally occurring allergen has been slightly modified by substitutions of single amino acids or nucleotides whereby the allergenic potential has been substantially maintained.

Allergen sources from which the allergenic proteins are derived may be major grass pollen, mite, bee venom or animal hair dander allergens. Specific examples of allergenic proteins are the group 1, group 2, group 4, group 5 group 6, group 11, group 12 and group 13 allergens of major grass pollen, Der p 1 and Der p 2 (mite), phospholipase from bee venom and Fel d 1 (cat).

In one embodiment the hybrid polypeptide comprises at least one complete allergenic protein. It may also comprise two different complete allergenic proteins. It is not only possible to combine different groups of allergenic grass pollen but also to combine allergenic proteins derived from different sources. In a particular embodiment all sequences of the hybrid polypeptide derived from allergenic proteins represent complete allergenic proteins.

In another embodiment the hybrid polypeptide comprises at least one fragment of an allergenic protein wherein the fragment consists of at least eight consecutive amino acids of the respective allergenic protein. Preferably the fragment consists of at least 12, more preferably of at least 20 and most preferably of at least 30 consecutive amino acids of the respective allergenic proteins. In another embodiment all amino acid sequences derived from allergenic proteins are fragments of at least eight consecutive amino acids of the respective allergenic proteins from which they are derived. The preferred length of these fragments is at least 12, more preferably at least 20, most preferably at least 30 consecutive amino acids of the respective allergenic protein.

When fragments of allergenic proteins are employed it is possible to prepare a hybrid polypeptide comprising only fragments which have an allergenic activity which is lower compared with the respective allergenic proteins from which they are derived. This effect may be due to the destruction of epitopes by modified secondary or tertiary structure of the fragment compared with the full length protein. In the most preferred embodiment, the hybrid polypeptide has an allergic activity which is lower than the allergenic activity of each of the allergenic proteins from which the hybrid polypeptide is derived. Usually, the allergenic activity of the hybrid polypeptide is less than 50% of that of each of the allergenic proteins from which the hybrid polypeptide is derived. In a particular embodiment, the hybrid polypeptide has substantially no allergenic activity.

According to the invention the allergenic activity of a sample is determined by determining the IgE antibodies which are induced in a test animal upon application of the sample. The allergenic activity is preferably defined in suitable in vitro or in vivo tests. A preferred in vitro test is the basophil histamine release assay as described in Vrtala et al., J. Clin. Invest. 1997, 99, pp. 1673-1681. Alternatively the allergenic activity is determined in a skin test as described in van Hage-Hamsten et al. J. Allergy Clin. Immunol. 1999, 104, pp. 969-977 or in Pauli et al. Clin. Exp. Allergy 2000, 30, pp. 1076-1084.

In one embodiment the hybrid polypeptide comprises two portions which are derived from two different allergenic proteins. The hybrid polypeptide of the invention, however, may comprise three, four, five or even more portions each of which is derived from a different allergenic protein.

The hybrid polypeptide of the invention does not necessarily consist only of amino acid sequences derived from allergenic proteins. It is possible that artificial sequences (e.g. spacer sequences) are inserted between the units representing sequences from different allergenic proteins. It is also possible that the amino acid sequences of the naturally occurring allergenic proteins are modified, e.g. by genetic engineering to introduce mutations which reduce the allergenic activity of the fragment. It is also preferred that the hybrid polypeptide comprises a "tag" sequence which facilitates the purification of the hybrid polypeptide upon expression in a host cell. An example of a "tag" is the hexahistidine tag which allows purification by $Ni^{2+}$ chelate chromatography. Other tags are known in the art.

The hybrid polypeptide of the invention may be prepared by several methods. In one embodiment the polypeptide is prepared by expressing a polynucleotide in a host cell. The host cell may be a procaryotic or a eucaryotic cell. If procaryotic cells are used the host is preferably E. coli. Examples of eucaryotic cells are yeast, insect cells or cell lines like CHO cells. After introducing a suitable polynucleotide encoding the polypeptide of the invention into a host cell the host cell is cultured under conditions such that the polypeptide is expressed in the cell. The polypeptide may be secreted by the cell or accumulate inside the cell. Known purification methods can be used to recover the hybrid polypeptide from the cell or from the culture medium.

The invention also encompasses the preparation of the hybrid polypeptide by chemical synthesis such as solid phase synthesis.

The invention further concerns a polynucleotide encoding a hybrid polypeptide according to the invention. Due to the degeneracy of the genetic code many different polynucleotide molecules may encode a single polypeptide. The polynucleotide of the invention preferably is an expression construct for obtaining the polypeptide after expression in host cells. The expression construct may further comprise components which are generally known in the art such as promoter sequences, genes encoding resistance factors against antibiotics, a replication origin etc.

The invention further relates to a cell transfected or transformed with a polynucleotide of the invention. The cell may be a eucaryotic cell or a procaryotic cell. Eucaryotic cells may be transfected by a method known per se such as calcium phosphate mediated transfection, electroporation, lipofection etc.

The invention further relates to a pharmaceutical composition containing a polypeptide, polynucleotide or a cell according to the invention. The pharmaceutical composition may further contain a pharmaceutically acceptable carrier or diluent such as a buffer or salt solution. Preferably the pharmaceutical composition of the invention is a vaccine composition. In a particular embodiment the pharmaceutical composition further contains an adjuvant such as $Al(OH)_3$.

The invention also relates to a method for the preparation of a hybrid polypeptide of the invention. The method comprises providing a polynucleotide encoding a hybrid polypeptide, introducing said polynucleotide into a host cell, culturing the host cell thus obtained under conditions such that the hybrid polypeptide is expressed, and recovering the expression product from the cell. The polynucleotide may be prepared by methods known in the art, it is preferred that PCR technology is used to prepare the polynucleotide encoding the hybrid polypeptide.

The invention further concerns the use of a hybrid polypeptide, of a polynucleotide or of a cell of the invention for the preparation of a medicament for the treatment of an allergic disorder.

Such a medicament may be composed of the polynucleotide encoding a hybride vaccine which can be used directly for DNA-based vaccination against Type I allergy. The recombinant or synthetic hybrid polypeptide may be used to prepare formulations for the oral, sublingual or parenteral treatment of Type I allergic disorders as they are now routinely used for immunotherapy. Examples are formulations for sublingual immunotherapy or adjuvant bound hybrid polypeptides for injection immunotherapy. Possible applications comprise also cell based forms of immunotherapy which may be based on e.g., dendritic cells or other antigen presenting cells. Those cells are transformed and express the antigen in vivo. Preferably autologous cells transformed with suitable vectors are used.

One mode of applications may be the subcutaneous injection of adjuvant-bound hybrid polypeptides. Another possibility is the oral or nasal administration of the hybrid polypeptide in order to induce immunological tolerance or anergy against the components of the hybrid polypeptides. All these possible formulations can be prepared according to rules (dosage, adjuvants, schemes of administration) which are known to the person skilled in the art.

The invention also relates to the use of a hybrid polypeptide, of a polynucleotide, or of a cell of the invention for the preparation of a medicament for prophylactic vaccination or tolerance induction. Prophylactic administration of hybride polypeptides means the administration of the polypeptide to individuals, preferentially children, who do not yet suffer from Type I allergy in order to induce a state of immunological tolerance, anergy or non-responsiveness, or a protective immunity against the components of the hybrid vaccine. This may be achieved by the various protocols outlined for treatment of an established allergic disorder. The prophylactic treatment may be performed with hybrid polypeptides consisting of hybride polypeptides or the polynucleotides coding for the hybrid polypeptides as outlined before.

In a further embodiment the invention relates to the use of a hybrid polypeptide of the invention for the detection of antibodies against an allergenic protein in a sample. The antibody may be an IgM, IgE, IgG or IgA antibody. The concentration of the antibody may be determined from a sample which has been obtained from a body fluid. The sample may be derived from animals or humans. Such tests may use a solid phase-immobilized hybrid polypeptide or the hybrid polypeptide in the fluid phase. Examples for such tests may be ELISA tests. Westernblotting tests or any other test where the hybrid polypeptide is immobilized to bind specific antibodies out from the test sample. Alternatively the hybrid polypeptide is added directly to the antibody-containing fluid in order to adsorb specific antibodies as e.g., is done for competitive immunological assays.

The polypeptide of the invention may also be used for cellular tests such as a T-cell proliferation test, mediator release test etc. The hybridpolypeptide may be exposed to various types of cells in order to elicit measurable responses. Such responses may comprise the release of histamine or other mediators (e.g., leukotriens, serotonine, ECP) in the case of allergic effector cells (e.g., basophils mast cells, eosinophils). In another type of assay the proliferation or death (e.g., apoptosis) of cells may be measured e.g., by the uptake of $^3H$ Thymidine or any other suitable assay. Such cells may be T cells. Furthermore, hybrid polypeptides may be used to induce the release of cytokines or other immunologically relevant substances (e.g., from T cells) that can be measured. Furthermore, they may be used for antigen presentation assays. The hybrid polypeptide of the invention may also be used for diagnostic screening purposes. Hybrid polypeptides may be also used for in vivo provocation testing. Such tests may comprise skin testing (e.g., skin prick or intradermal testing), nasal provocation testing, all forms of food challenge testing or bronchial provocation testing.

Since hybrid polypeptides can contain epitopes of unrelated allergens they may be used for diagnostic screening tests (in vitro, in vivo as outlined above) in order to detect sensitization or unresponsiveness against one of the components of the hybrid polypeptide. This may allow to provide the physician with a diagnostic test which is suited to screen for sensitized patients in a fast way. Currently such tests (e.g., Phadiatop, Pharmacia, Uppsala, Sweden) consist of a mixture of non-covalently bound allergens which are coupled to one carrier. Therefore, the coupling rate of the individual components is difficult to control whereas a hybrid polypeptide would represent a preferential formulation for the preparation of such a screening test.

More than 40% of allergic patients are sensitized to grass pollens from different species. Grasses are also important allergen sources because of their worldwide distribution and heavy pollen production. They contain a variety of different allergenic components which occur as crossreactive allergens in different monocots. The inventors demonstrated that it is possible to generate by recombinant DNA technology hybrid allergens which consist of immunologically unrelated allergens and their epitopes.

In a first step frequent co-sensitizations were determined using purified recombinant timothy grass pollen allergens to select the most frequently recognized allergen combinations for the hybrid allergen approach. According to the pilot experiments hybrids consisting of immunologically unrelated major timothy grass pollen allergens were engineered. They comprised hybrids of the major timothy grass pollen allergens Phl p 5/Phl p 1, Phl p 2/Phl p 6 and a combination of all four molecules. As demonstrated for Phl p 2/Phl p 6 we found no evidence that a certain order of engineering the individual components would affect the presentation of epitopes. Both, the rPhl p 2/Phl p 6 hybrid and the rPhl p 6/Phl p 2 hybrid preserved the relevant B and T cell epitopes of the components. The giant consisting of all 4 allergens also contained the relevant epitopes of the single components.

The hybrid allergen approach will open new avenues for diagnosis and treatment of Type I allergy. Hybrids consisting of the most frequently recognized allergens with preserved epitopes represent candidate molecules for in vitro as well as in vivo allergy screening tests. The giant described in the present application will likely identify more than 95% of timothy grass pollen allergic patients when used for diagnosis, because it resembles most of the relevant IgE epitopes present in natural timothy grass pollen extract. Molecules such as the giant can be produced also for other allergen systems (e.g., mite allergy). The advantage of using hybrid allergens for diagnosis is that they can be produced in a well controlled manner. In contrast to natural allergen extracts, which consist of a difficult to standardize mixture of allergens and non-allergenic materials, hybrid allergens will contain the relevant epitopes in a well defined ratio.

Recombinant hybrid allergens can also be used for immunotherapy. They can either be composed of the biologically active components or of hypoallergenic allergen units. Hybrid allergens covering frequent co-sensitization patterns may then be used for the treatment of allergies to complex allergen sources, e.g., grass pollen allergy because they resemble the relevant epitopes of the complete extract. Since the hybrid allergens consist of defined components it will be possible to produce well defined formulations for vaccination treatment. Hybrid allergens produced out of hypoallergenic variants will be tolerated in high doses and thus can be used like vaccines regularly used for prevention of viral infections. In this respect it may be considered to use hybrid allergens containing the epitopes of the most relevant allergens for prophylactic vaccination or tolerance induction even in not yet sensitized individuals.

The fact that the fusion of different antigenic components in form of a hybrid molecule increased the immunogenicity of the individual components has several implications for allergen-specific immunotherapy and for vaccination in general. Allergens or antigens against which immune responses are desired and which per se exhibit low immunogenicity can be fused to hybrids to increase their immunogenicity without using other carrier proteins or adjuvants. This principle will allow to induce high levels of protective antibody responses against allergens, allergen fragments, allergen epitopes or mimicks thereof. Using this principle it is also possible to increase the immune response towards antigens/epitopes derived from infectious agents, tumors or other components against which it is difficult to induce immune responses.

DESCRIPTION OF THE TABLES AND FIGURES

Table 1 shows the percentage inhibition of IgE binding to recombinant Phl p 2 and Phl p 6 achieved after preadsorption of sera from 20 patients with the hybrid allergens (rPhl p 2/rPhl p 6, rPhl p 6/rPhl p 2) or the recombinant allergens (rPhl p 2, rPhl p 6).

Table 2 shows the percentage inhibition of IgE binding to recombinant Phl p 1, Phl p 5, and Bet v 1 achieved after preadsorption of sera from 20 patients with the hybrid allergen rPhl p 5/rPhl p 1 or the recombinant allergens (rPhl p 1, rPhl p 5, and rBet v 1).

Table 3. Mouse antisera raised against hybrid molecules inhibit the binding of grass pollen allergic patients IgE to the individual allergens. ELISA plate-bound allergens (A: rPhl p 2 and rPhl p 6; B: rPhl p 1 and rPhl p 5) were preincubated with mouse antisera (mouse anti-rP2-P6, anti-rP6-P2, anti-rPhl p 2, anti-rPhl p 6, anti-rP5-P1, anti-rPhl p 1, anti-rPhl p 5. The percentages inhibition of IgE binding obtained for 4 grass pollen allergic patients are displayed.

FIG. 1 shows the frequency of co-sensitization to timothy grass pollen allergens rPhl p 1, rPhl p 2, rPhl p 5, and rPhl p 6 as determined in a population of 110 grass pollen allergic patients.

FIG. 2 outlines the construction of hybrid vaccines. The fusion of the two genes (e.g. Phl p 5, Phl p 1) is mediated by a two-step PCR reaction, creating overlapping ends in the first PCR reaction followed by the amplification of both sequences in a second PCR step.

FIG. 3 shows the result of example 3. Purified timothy grass pollen allergens (rPhl p 1, rPhl p 2, rPhl p 5, and rPhl p 6) and hybrids of them (rPhl p 5/rPhl p 1, rPhl p 2/rPhl p 6, and rPhl p 6/rPhl p 2) were loaded on a SDS polyacrylamide gel and stained with Coomassie brilliant blue. Molecular weights are displayed at the left margin.

In FIG. 4(A) a purified recombinant hybrid consisting of Phl p 6/Phl p 2/Phl p 5/Phl p 1 was dotted on nitrocellulose filters. In row (B) rPhl p 2 (lane 1,3,4, and 5) and rPhl p 5 (lane 2) was immobilized. Filters were incubated with rabbit antisera against rPhl p 1 (lane 1), rPhl p 2 (lane 2), rPhl p 5 (lane 3), and rPhl p 6 (lane 4). The filter in lane 5 was exposed to a mouse monoclonal anti-His-tag antibody.

FIGS. 5 to 7 show that recombinant hybrid molecules induce stronger $IgG_1$ antibody responses in mice than the individual components or mixtures thereof.

FIG. 5. ELISA plate-bound purified recombinant allergens (A: rPhl p 2; B: rPhl p 6; C: rPhl p 1; D: rPhl p 5) were incubated with sera from mice (8 mice per group) which had been immunized with the hybrid molecules (rP2-P6, rP6-P2, rP5-P1), the individual recombinant allergens (rPhl p 1, rPhl p 2, rPhl p 5, rPhl p 6), or with timothy grass pollen extract as indicated on the x-axis. Mean $IgG_1$ levels of sera collected 4 and 8 weeks after immunization correspond to the OD values displayed on the y-axis.

FIG. 6. ELISA plate-bound purified recombinant allergens (rPhl p 1, rPhl p 2, rPhl p 5, rPhl p 6) were incubated with sera from mice (8 mice per group) which had been immunized with (A) the giant molecule or the individual recombinant allergens rPhl p 1, rPhl p 2, rPhl p 5, rPhl p 6, and with (B) the giant molecule or an equimolar mixture of rPhl p 1, rPhl p 2, rPhl p 5, and rPhl p 6 as indicated on the x-axis. Mean $IgG_1$ levels of sera collected 4 and 8 weeks after immunization correspond to the OD values displayed on the y-axis.

Figure 7:
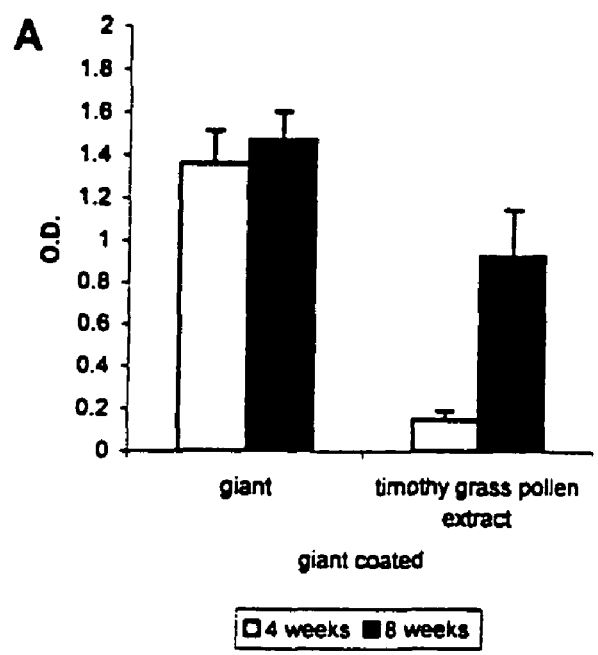
Figure 7:
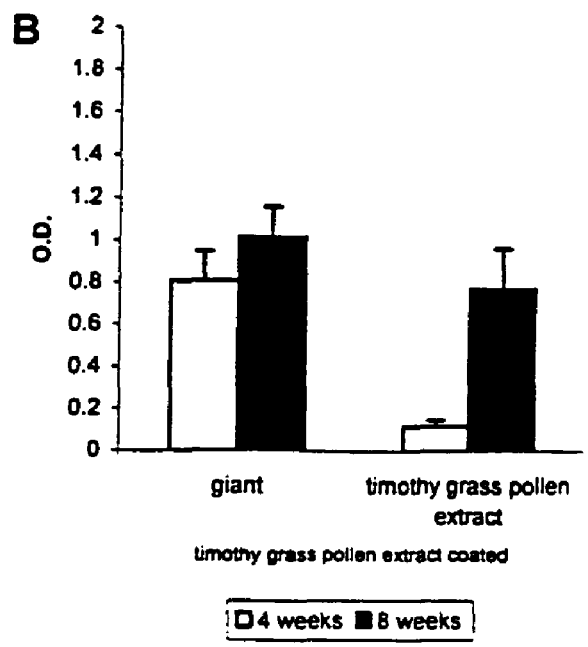

FIG. 7. The ELISA plate-bound giant (A), and timothy grass pollen extract (B) were incubated with sera from mice (8 mice per group) which had been immunized with the giant or timothy grass pollen extract as indicated on the x-axis. Mean $IgG_1$ levels of sera collected 4 and 8 weeks after immunization correspond to the OD values displayed on the y-axis.

The following examples further illustrate the invention:

EXAMPLE 1

Determination of Frequent Co-Sensitization Patterns

Grasspollen contain a variety of immunologically distinct and related allergens. These components are recognized at different frequencies and intensities. Recombinant timothy grass pollen allergens, rPhl p 1, rPhl p 2, rPhl p 5, and rPhl p 6, were previously identified as the most important components which resemble most of the IgE epitopes of natural grass pollen extracts (Niederberger et al. (1998) IgE antibodies to recombinant pollen allergens (Phl p 1, Phl p 2, Phl p 5, and Bet v 2) account for a high percentage of grass pollen-specific IgE. J Allergy Clin Immunol 101: 258-264). The results of the evaluation of co-sensitizations in 110 grass pollen allergic patients to combinations of the recombinant timothy grass pollen allergens are displayed in FIG. 1. ELISA testing with purified recombinant allergens showed that 60% percent of the patients were co-sensitized to rPhl p 1 and rPhl p 5, 30% contained IgE antibodies to rPhl p 2 and rPhl p 6 and 30% reacted simultaneously to all four recombinant allergens (FIG. 1). Previous competition studies had indicated that a mixture of the above four allergens contained the majority of IgE epitopes present in 8 different monocot pollens (grasses, corn) (Laffer et al. (1996) Comparison of recombinant timothy grass pollen allergens with natural extract for diagnosis of grass pollen allergy in different populations. J Allergy Clin Immunol; 98: 652-658).

Patients Sera, Antisera and Recombinant Allergens:

Sera of 110 allergic patients were characterized by a positive timothy grass pollen RAST (radioallergosorbent test) result and by determination of IgE antibodies to timothy grass pollen extract by Western blotting as described (Niederberger et al. (1998) J Allergy Clin Immunol 101: 258-264). The recombinant timothy grass pollen allergens rPhl p 1, rPhl p 2, rPhl p 5, and rPhl p 6 were purified as described previously (Vrtala et al. (1995) J. Allergy Clin. Immunol 97: 781-787; Vrtala et al. (1999) J. Immunol. 163:5489-5496). The rabbit anti-rPhl p 1, anti-rPhl p 2, anti-rPhl p 5, and anti-rPhl p 6 antisera were raised against purified rPhl p 1, rPhl p 2, rPhl p 5, and rPhl p 6 using CFA (Charles River, Kissleg, Germany).

EXAMPLE 2

Construction of Recombinant Hybrid Allergens

The protocol for the construction of recombinant hybrid allergens is displayed in FIG. 2. As exemplified for a hybrid consisting of rPhl p 5 linked to rPhl p 1, cDNAs coding for the components are amplified with suitable primer pairs (FIG. 2: Phl p 5: w, x; Phl p 1: y, z) in order to create overlapping ends. In a subsequent second PCR reaction, a cDNA comprising both cDNAs is created with primers specific for the 5' end of the first cDNA (Phl p 5: w) and the 3' end of the second cDNA (Phl p 1: z) using both PCR products of the first reactions as templates. Using this technology we produced recombinant hybrids consisting of a combination of Phl p 5/Phl p 1, rPhl p 2/rPhl p 6, rPhl p 6/rPhl p 2 and of all four allergens (N-terminus-rPhl p 6-rPhl p 2-rPhl p 5-rPhl p 1-C-terminus), the latter referred to as the "giant".

Construction of expression plasmids for rPhl p 5/rPhl p 1-, rPhl p 2/rPhl p 6-, rPhl p 6/rPhl p 2-, and rPhl p 6/rPhl p 2/rPhl p 5/rPhl p 1 hybrid proteins:

The cDNAs of Phl p 5 and Phl p 1 were obtained by polymerase chain reaction using the primers 5' GGA ATT CAT ATG GCC GAT CTC GGT TAC 3' (SEQ ID NO: 1) and 5' CGG GGT ACC GAC TTT GTA GCC ACC AGT 3' (SEQ ID NO: 2) for Phl p 5 and 5' CGG GGT ACC ATG ATC CCC MG GTT CCC 3' (SEQ ID NO: 3) and 5' CGG GAT CCT CAG TGG TGG TGG TGG TGG TGC TTG ACT CGT AG CTG GT 3' (SEQ ID NO: 4) for Phl p 1. The signal peptide of Phl p 5 was replaced by a NdeI restriction site, containing the ATG start codon at the 5' end of the coding region. A KpnI restriction site was introduced at the 3' end of Phl p 5 replacing the stop-codon. The Phl p 1 sequence, lacking the signal peptide, started with a KpnI restriction site at the 5' end. At the 3' end a nucleotide street coding for a Hexahistidine-tag was introduced, followed by a stop codon and a BamHI restriction site. The PCR products were inserted as NdeI/KpnI/BamHI fragment into a pET17b expression vector.

The Phl p 2/Phl p 6 and Phl p 6/Phl p 2 sequences were constructed using PCR based 'gene soeing' (17). In a first PCR reaction the cDNAs of Phl p 2 and Phl p 6 were amplified using the primers 5' GGA ATT CAT ATG GTG CCG MG GTG ACG 3' (SEQ ID NO: 5), and 5' CGT GGC CTT CCC CAT MG CTT CTC TTC TGG CGC GTA GGT 3' (SEQ ID NO: 6) for Phl p 2 and 5' MG CTT ATG GGG MG GCC ACG ACC 3' (SEQ ID NO: 7) and 5' C GGG ATC CTA GTG GTG GTG GTG GTG GTG CGC GCC GGG CTT GAC AGC 3' (SEQ ID NO: 8) for Phl p 6 to create overlapping ends. In a subsequent PCR reaction the two agarose gel purified PCR products (using QIAGEN gel purification kit) were used as templates and amplified using the primers 5' GGA ATT CAT ATG GTG CCG MG GTG ACG 3' (SEQ ID NO: 9) and 5' C GGG ATC CTA GTG GTG GTG GTG GTG GTG CGC GCC GGG CTT GAC AGC 3' (SEQ ID NO: 10). The signal peptide of Phl p 2 was replaced by a NdeI restriction site at the 5' end, the stop codon at the 3' end was removed. In the Phi p 6 sequence, also lacking the signal peptide, a Hexahistidine tag was introduced followed by a stop codon and a BamHI restriction site. The resulting Phl p 2/Phl p 6 construct was inserted as a NdeI/BamHI fragment into the pET17b expression vector.

The Phl p 6/Phl p 2 sequence was constructed using the same method with the PCR primers 5' GGA ATT CAT ATG GGG MG GCC ACG ACC GAG 3' (SEQ ID NO: 11) and 5' CAC CTT CGG CAC CAT MG CTT CGC GCC GGG CTT GAC AGC 3' (SEQ ID NO: 12) for Phl p 6 and 5' MG CTT ATG GTG CCG MG GTG ACG 3' (SEQ ID NO: 13) and 5' C GGG ATC CTA GTG GTG GTG GTG GTG GTG CTC TTC TGG CGC GTA GGT 3' (SEQ ID NO: 14) for Phl p 2 in the first PCR reaction and the primers 5' GGA ATT CAT ATG GGG MG GCC ACG ACC GAG 3' (SEQ ID NO: 15) and 5' C GGG ATC CTA GTG GTG GTG GTG GTG GTG CTC TTC TGG CGC GTA GGT 3' (SEQ ID NO: 16) for the second PCR reaction. The resulting Phl p 6/Phl p 2 construct was inserted in the pET17b vector as a NdeI/BamHI fragment.

For the construction of the Phl p 6/Phl p 2/Phl p 5/Phl p 1 hybrid ("giant") the Phl p 6/Phl p 2 construct was taken as a template in a PCR reaction using the primers 5' GGA ATT CAT ATG GGG MG GCC ACG ACC GAG 3' (SEQ ID NO: 17) and 5' GGG ATT TCC ATA TGC TCT TCT GGC GCG TAG G 3' (SEQ ID NO: 18) replacing the 3' Hexahistidine tag and the stop codon by an NdeI restriction site. The sequence was cloned into the pET17b vector, containing the Phl p 5/Phl p 1 construct as a NdeI fragment. The right orientation of the insert was examined by restriction digest.

EXAMPLE 3

Expression and Purification of Hybrid Allergens

Recombinant hybrid allergens with a C-terminal hexahistidine tag were expressed in *E. coli* BL21 (DE3) and purified by Nickel affinity chromatography. The rPhl p 2/rPhl p 6 and rPhl p 6/rPhl p 2 hybrid were purified from the soluble cytoplasmic fraction of *E. coli* extracts whereas the rPhl p 5/rPhl p 1 hybrid and the "giant" were solubilized from the insoluble inclusion body fraction of *E. coli* in urea. FIG. 3 shows a Coomassie-stained SDS-PAGE containing three of the hybrids and the single recombinant allergens. The molecular mass determined by SDS-PAGE corresponded to the molecular weight calculated for the hybrids on the basis of their deduced amino acid sequence (rPh l p 5/rPhl p 1:60 kDa; rPhl p 2/rPhl p 6 and rPhl p 6/rPhl p 2:22 kDa; "giant": 82 kDa; data not shown).

Experimental Protocol:

All constructs were expressed in *E. coli* BL21 (DE3). Cells were grown in LB-medium containing 100 mg/l ampicillin to an $OD_{600}$ of 0.8. The expression of the recombinant proteins was induced by adding isopropyl-β-thiogalactopyranoside (IPTG) to a final concentration of 0.5 mM. After 4 hours at 37° C. cells were harvested by centrifugation.

rPhl p 2/rPhl p 6 and rPhl p 6/rPhl p 2 were expressed as soluble proteins. Cells were resuspended in lysis buffer (50 mM $NaH_2PO_4$, 300 mM NaCl, 10 mM imidazole, pH 8.0) and lysed with an ultraturrax (Polytron, Kinematica AG, Switzerland). The lysate was centrifuged at 10,000×g for 30 min at 4° C. to pellet the cellular debris. The supernatant was loaded on a Ni-NTA column (QIAGEN), the proteins were eluted with 250 mM imidazole and dialyzed against water.

rPhl p 5/rPhl p 1 and rPhl p 6/rPhl p 2/rPhl p 5/rPhl p 1 were expressed in the inclusion body fraction. Cells were resuspended in 10 mM Tris, 0.1% Triton, pH 7.4 and lysed by adding lysozyme to 1 mg/ml. After centrifugation at 14 000×g for 20 min at 4° C. the pellet was washed 4× with 5 mM Tris pH 8.0, 0.05M NaCl, 0.25% Desoxicholate, 0.25 mM β-Mercaptoethanol and once with 10 mM Tris, pH 8.0, 3% isopropanole. Inclusion bodies were solubilized with 8M urea, 100 mM $NaH_2PO_4$, 10 mM Tris, pH 8.0. After centrifugation at 14 000×g for 20 min the supernatant was loaded on a Ni-NTA column (Qiagen). The proteins were renatured on the column using a linear 6M-1M urea gradient in 500 mM NaCl, 20% glycerol, 20 mM Tris, pH 7.4) over a period of 1.5 h (18). Proteins were eluted by addition of 250 mM imidazole and dialyzed against PBS pH 7.4.

EXAMPLE 4

Hybrid Allergens Contain the Relevant Epitopes of Their Components

Figure 4:

Recombinant hybrid allergens contained the complete primary amino acid sequences of their components and thus the complete repertoire of T cell epitopes of the single allergens. The presence of B cell epitopes was investigated with antibodies of predefined specificity for the individual components and by immunological competition experiments. FIG. 4 shows that the "giant" is recognized by antisera raised against rPh l p 1, rPhl p 2, rPhl p 5 and rPhl p 6, respectively (FIG. 4, row A: 1-4). The correct expression of the C-terminal hexahistidine tag was demonstrated by the reactivity of a mouse monoclonal anti-Histag antibody which specifically recognized the "Giant (FIG. 4: row A, 5) but not rPhl p 2 containing no hexahistidine tag (FIG. 4: row B, 5). Recombinant Phl p 2 (row B: 1, 3, 4) and rPhl p 5 (row B: 2) (negative controls) did not react with the antisera (FIG. 4: row B).

Next we investigated whether the hybrid allergens can be used to block the binding of grass pollen allergic patients (n=20) IgE antibodies to the individual components (Tables 1, 2). Table 1 shows that the rPhl p 2/rPhl p 6 as well as the rPhl p 6/rPhl p 2 hybrid inhibited IgE binding to both of the components (rPhl p 2, rPhl p 6) in a comparable manner as the single recombinant allergens (approximately 80% inhibition of IgE binding). Likewise, we found that the rPhl p 5/rPhl p 1 hybrid inhibited IgE binding of the 20 patients to both, rPhl p 1 and rPhl p 5, as efficient as the single components (average inhibition 85%) (Table 2). No inhibition was observed when sera were preadsorbed with the rPhl p 5/rPhl p 1 hybrid and reacted with an unrelated allergen (major birch pollen allergen, Bet v 1) whereas rBet v 1 caused almost complete autoinhibition (83% inhibition) (Table 2).

Experimental Protocol:

ELISA Competition Experiments:

Sera from 20 patients were diluted 1:10 in Tris-buffered saline (TBS) for the inhibition with rPhl p 5/rPhl p 1 and 1:5 for inhibition with rPhl p 2/rPhl p 6 and rPhl p 6/rPhl p 2. The sera were preadsorbed overnight at 4° C. either recombinant Phl p 1, Phl p 5, Phl p 5/Phl p 1, Phl p 2, Phl p 6, Phl p 2/Phl p 6, Phl p 6/Phl p 2, Bet v 1, or BSA (10 μg/ml). ELISA plates were coated with recombinant Phl p 1, Phl p 2, Phl p 5, Phl p 6, and Bet v 1 (5 μg/ml) at 4° C. overnight. The ELISA was performed as described (Niederberger et al. (1998) J Allergy Clin Immunol 101: 258-264).

Dot Blots:

Aliquots of approximately 1 μg of purified, recombinant Phl p 6/Phl p 2/Phl p 5/Phl p 1, and rPhl p 5 and rPhl p 2 as negative controls, were dotted on nitrocellulose membranes. Filters were blocked with TBS, 1% BSA, 0.05% Tween-20 for 1 hour and incubated with rabbit anti-Phl p 1, anti-Phl p 5 (diluted 1:5000), anti-Phl p 2 (diluted 1:500), anti-Phl p 6 (diluted 1:2000) sera, and a mouse monoclonal anti-Hexahistidin Ab (Dianova, Germany) diluted 1:1000 in TBS, 1% BSA, 0.05% Tween-20. Filters were washed 3× with TBS, 0.05% Tween-20, incubated with a secondary alkaline phosphatase-coupled goat anti-rabbit IgG antibody (Jackson) and for the His-tag detection with a alkaline phosphatase-coupled anti-mouse IgG antibody (PharMingen) diluted 1:1000 in TBS, 1% BSA, 0.05% Tween-20 for 1 hour, and washed 3× with TBS, 0.05% Tween-20. Colour reaction was started by adding NBT/BCIP (300 μg/ml) and stopped by the addition of water.

EXAMPLE 5

Figure 5:
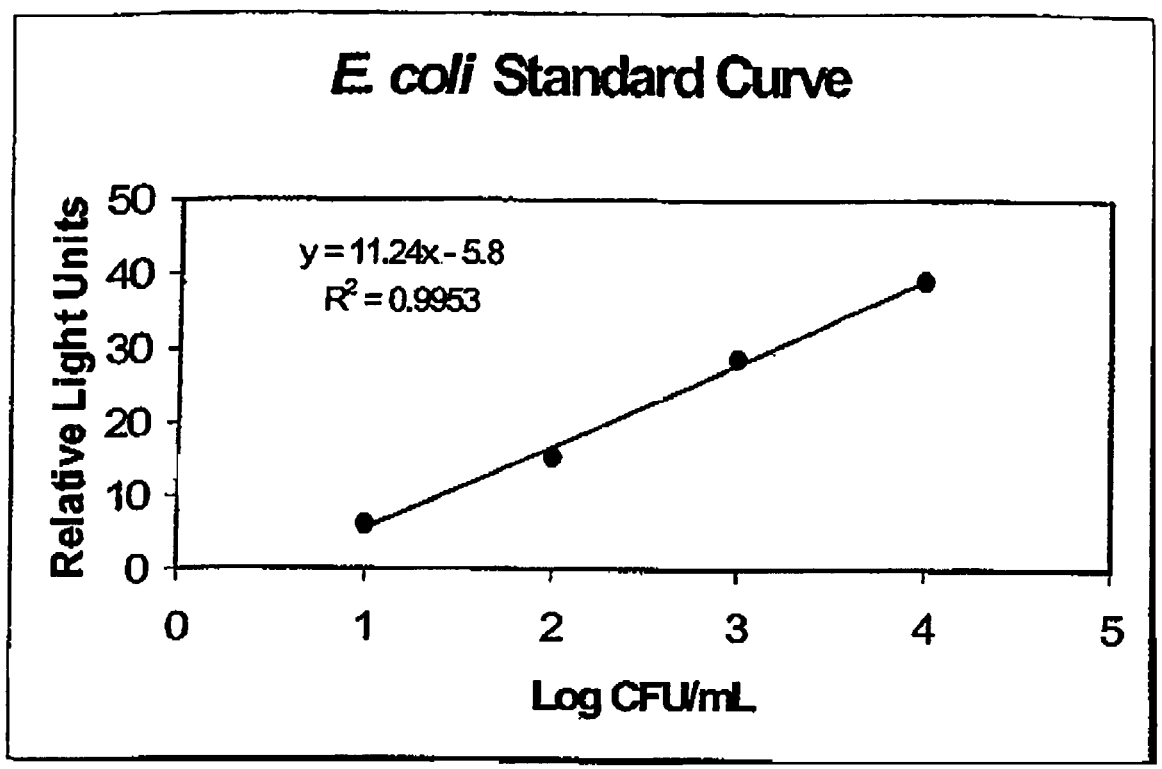

Hybridmolecules Induce Stronger Immune Responses in Mice than the Individual Components or Mixtures Thereof To evaluate wether immunization with the hybrid allergens induces IgG antibodies that recognize the individual allergen components, groups of 8 mice each were immunized with the hybrids, the individual allergens or timothy grass pollen extract. FIG. 5 demonstrates that the average IgG$_1$ responses induced by the hybrid molecules to each of the individual allergens (rPhl p 1, rPhl p 2, rPhl p 5, or rPhl p 6) were higher than those obtained by immunization with the single allergen components. High IgG$_1$ antibody levels induced by the hybrids were already detectable 4 weeks after the first immunization and had increased further after 4 more weeks. Perhaps most interesting was the finding that the hybrid molecules induced higher IgG$_1$ levels to the individual allergen components than timothy grass pollen extract (FIG. 5). The latter was particularly evident for Phl p 2, Phl p 6 and Phl p 1 which were poorly recognized by extract-induced antibodies, whereas the hybrid molecules induced vigorous anti-Phl p 1-, anti-Phl p 2- and anti-Phl p 6 antibody responses (FIG. 5).

Figure 6:
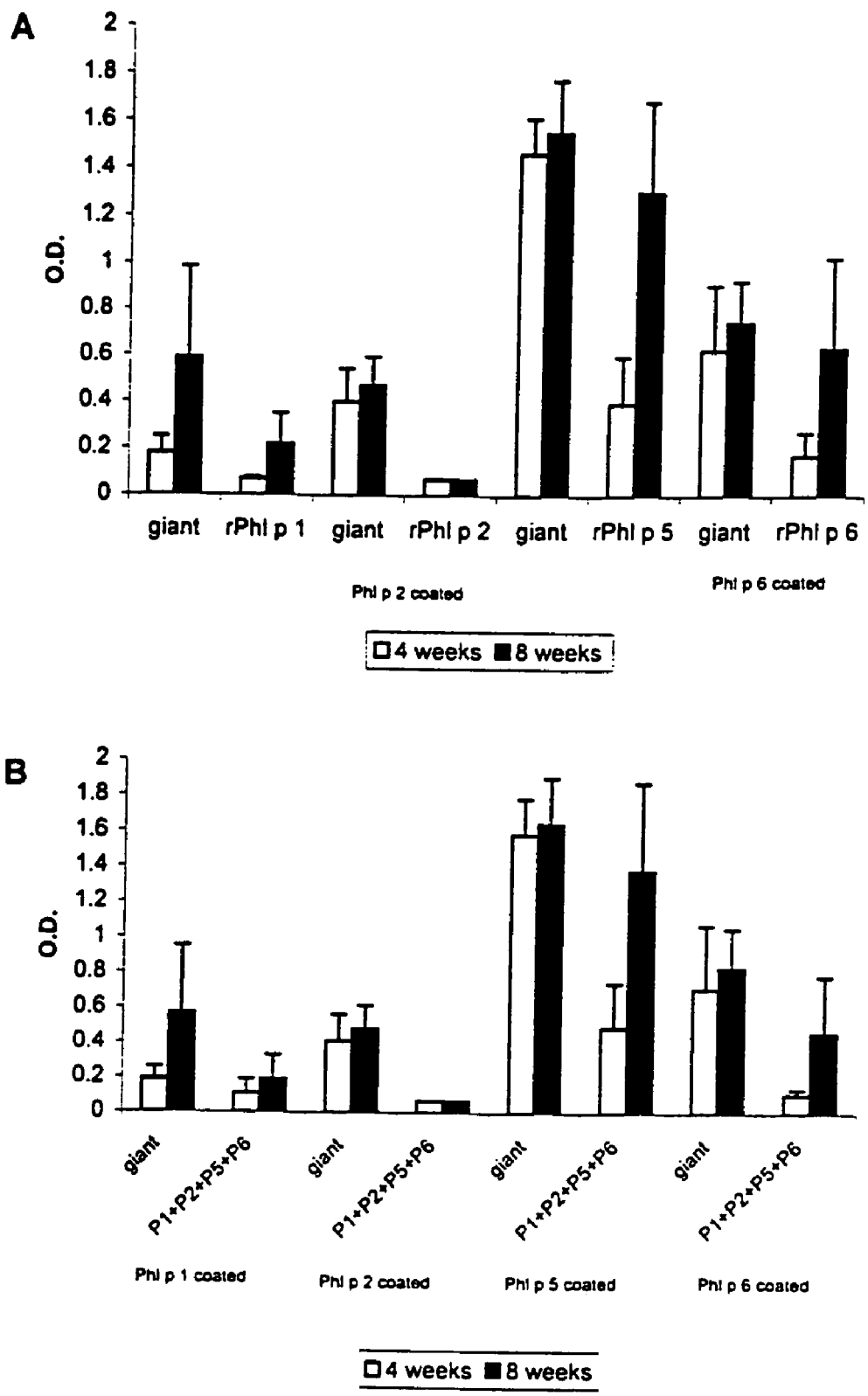

Likewise we found that immunization with the giant molecule induced stronger antibody responses to each of the components (Phl p 1, Phl p 2, Phl p 5, Phl p 6) than immunization with the individual antigens (FIG. 6A) or an equimolar mixture of the antigens (FIG. 6B). Immunization with the giant yielded also better immune responses than immunization with timothy grass pollen extract. IgG antibodies induced with timothy grass pollen extract exhibited lower reactivity to the giant and to the extract than those induced with the giant (FIGS. 7A, B).

Immunization of Mice and Measurement of Specific Antibody Levels

Groups of 8 female BALB/c mice (age: 8 weeks) (Charles River, Germany) were immunized subcutaneously with rPhl p 1, rPhl p 2, rPhl p 5, rPhl p 6, rP2-P6, rP6-P2, rP5-P1, the giant molecule, timothy grass pollen extract, or an equimolar mixture of rPhl p 1, rPhl p 2, rPhl p 5, and rPhl p 6 adsorbed to Al(OH)$_3$ (Alu-Gel-S, Serva, Ingelheim, Germany). Animals were maintained in the animal care unit of the Institute of Pathophysiology, University of Vienna, according to the local guidelines for animal care. Mice were immunized and bled from the tail veins in four-week intervals and sera were stored at −20° C. until analysis.

IgG$_1$ responses against rPhl p 1, rPhl p 2, rPhl p 5, rPhl p 6, rP2-P6, rP6-P2, rP5-P1, the giant molecule, an equimolar mixture of rPhl p 1, rPhl p 2, rPhl p 5, and rPhl p 6, and timothy grass pollen extract were measured by ELISA. Allergens (recombinant allergens: 5 µg/ml; extract: 50 µg/ml) were coated to Nunc Maxisorp plates (Roskilde, Denmark) and incubated with 1:1000 diluted mouse-sera. Bound antibodies were detected with a 1:1000 diluted monoclonal rat anti-mouse IgG$_1$ (Pharmingen, San Diego, Calif., USA) and a 1:2000 diluted HRP-labeled sheep anti-rat antiserum (Amersham, Buckinghamshire, UK).

EXAMPLE 6

Hybrid Molecules Induce Protective Antibody Responses that Block the Binding of Allergic Patients' IgE to Grass Pollen Allergens Next we examined whether mouse antibodies induced with the hybrid molecules can block the binding of grass pollen allergic patients IgE antibodies to purified grass pollen allergens (Table 3). ELISA competition experiments performed with sera from 4 representative grass pollen allergic patients showed that antibodies induced by the hybrid molecules strongly inhibited IgE binding to the purified allergens: IgG antibodies induced with the rP2-P6 and the rP6-P2 hybrid molecule caused a 48%-54% inhibition of IgE binding to Phl p 2 and a 54%-67% inhibition of IgE binding to Phl p 6 (Table 3A). By contrast, the inhibition of IgE reactivity yielded by preincubation with antibodies induced with rPhl p 2 and rPhl p 6 alone was very low (0-15%) (Table 3A). Anti-P5-P1 antibodies caused a more than double inhibition of IgE binding to Phl p 5 (59.5% average inhibition) than antibodies raised against Phl p 5 alone (28%) (Table 3B). The inhibition of IgE binding to Phl p 1 yielded with the antibodies raised against the rP5-P1 hybrid (18.5% average inhibition) and Phl p 1 alone (29.5% average inhibition) were lower (Table 3B).

Similar results were obtained with the giant molecule which induced IgG antibodies that efficiently blocked the binding of grass pollen allergic patients IgE to Phl p 1, Phl p 2, Phl p 5, Phl p 6 and timothy grass pollen extract (data not shown).

ELISA for Assessment of Blocking Antibody Activity

The ability of the mouse anti-rP2-P6, anti-rP6-P2, and anti-rP5-P1 antibodies to inhibit the binding of grass pollen allergic patients' IgE Abs to rPhl p 1, rPhl p 2, rPhl p 5, or rPhl p 6 was examined by ELISA competition experiments. Recombinant Phl p 1, Phl p 2, Phl p 5, and Phl p 6 (1 µg/ml) were coated to ELISA plates (Nunc) over night at 4° C., plates were washed twice with TBST (Tris-buffered saline, 0.05% Tween), saturated with 200 µl TBST/1% BSA, and preincubated with mouse anti-rP2-P6, anti-rP6-P2, and anti-rP5-P1 antisera or, for control purposes, with the corresponding preimmune sera each diluted 1:50 in TBST/0.5% BSA overnight at 4° C. After washing 5 times with TBST, plates were incubated with human sera from grass pollen allergic patients diluted 1:5 in TBST/0.5% BSA over night at 4° C. After washing 5 times with TBST, bound human IgE was detected with an AP-labeled mouse anti-human IgE Ab (Pharmingen) diluted 1:1000 in TBST/0.5% BSA (1 hour at 37° C., 1 hour at 4° C.). After washing 5 times with TBST, the colour reaction was started by adding 100 µl ELISA substrate (Sigma Diagnostics, Inc., St. Louis, USA) The percentage of reduction of human IgE binding after preincubation with mouse antisera was determined according to the formula: % inhibition of IgE binding=$100-OD_I/OD_P \times 100$. $OD_I$ and $OD_P$ represent the extinctions after preincubation with the immune serum and the preimmune serum, respectively.

TABLE 1

| Patient | rPhl p 2 | rPhl p 2/ rPhl p 6 | rPhl p 6/ rPhl p 2 | rPhl p 6 | rPhl p 2/ rPhl p 6 | rPhl p 6/ rPhl p 2 |
|---|---|---|---|---|---|---|
| | rPhl p 2 coated | | | rPhl p 6 coated | | |
| 1 | 69 | 72 | 78 | 72 | 72 | 73 |
| 2 | 72 | 78 | 81 | 81 | 80 | 81 |
| 3 | 97 | 95 | 98 | 93 | 91 | 97 |
| 4 | 93 | 93 | 94 | 80 | 80 | 80 |
| 5 | 79 | 79 | 78 | 69 | 76 | 75 |
| 6 | 44 | 44 | 45 | 80 | 82 | 82 |
| 7 | 97 | 97 | 97 | 87 | 97 | 96 |
| 8 | 92 | 93 | 92 | 84 | 93 | 93 |
| 9 | 84 | 85 | 85 | 64 | 68 | 68 |
| 10 | 53 | 56 | 56 | 45 | 53 | 52 |
| 11 | 83 | 84 | 82 | 78 | 93 | 91 |
| 12 | 67 | 64 | 65 | 70 | 72 | 71 |
| 13 | 90 | 89 | 89 | 86 | 91 | 91 |
| 14 | 94 | 94 | 93 | 85 | 89 | 89 |
| 15 | 81 | 81 | 81 | 86 | 89 | 95 |
| 16 | 97 | 96 | 97 | 95 | 96 | 96 |
| 17 | 97 | 97 | 94 | 95 | 97 | 97 |
| 18 | 90 | 90 | 91 | 43 | 53 | 52 |
| 19 | 76 | 75 | 76 | 68 | 83 | 82 |
| 20 | 97 | 97 | 97 | 73 | 89 | 89 |
| mean | 83 | 83 | 84 | 77 | 82 | 83 |

TABLE 2

| Patient | rPhl p 1 | rPhl p 5/ rPhl p 1 | rPhl p 5 | rPhl p 5/ rPhl p 1 | rBet v 1 | rPhl p 5/ rPhl p 1 |
|---|---|---|---|---|---|---|
| 1 | 77 | 81 | 85 | 83 | 74 | 0 |
| 2 | 90 | 89 | 94 | 92 | 96 | 18 |
| 3 | 96 | 92 | 96 | 92 | 67 | 0 |
| 4 | 92 | 92 | 95 | 90 | - | - |
| 5 | 82 | 84 | 87 | 87 | - | - |
| 6 | 92 | 93 | 93 | 93 | 75 | 9 |
| 7 | 88 | 90 | 90 | 91 | 97 | 0 |
| 8 | 90 | 91 | 93 | 92 | 88 | 2 |
| 9 | 50 | 52 | 57 | 57 | 59 | 4 |
| 10 | 89 | 89 | 93 | 90 | 58 | 5 |
| 11 | 88 | 95 | 89 | 94 | - | - |
| 12 | 95 | 95 | 95 | 96 | 97 | 0 |
| 13 | 94 | 96 | 94 | 95 | 97 | 0 |
| 14 | 95 | 96 | 95 | 95 | 98 | 0 |
| 15 | 78 | 78 | 81 | 79 | 92 | 0 |
| 16 | 94 | 95 | 95 | 94 | 94 | 0 |
| 17 | 46 | 58 | 66 | 65 | - | - |
| 18 | 77 | 78 | 86 | 85 | 63 | 42 |
| 19 | 91 | 91 | 94 | 93 | - | - |
| 20 | 95 | 93 | 97 | 95 | 96 | 32 |
| mean | 85 | 86 | 89 | 88 | 83 | 7 |
|  | rPhl p 1 coated |  | rPhl p 5 coated |  | rBet v 1 coated |  |

TABLE 3

% Inhibition of IgE Binding to

A

| with | rPhl p 2 mouse anti-rP2-P6 | rPhl p 6 mouse anti-rP6-P2 | rPhl p 2 | rPhl p 6 | rPhl p 2 mouse anti-rPhl p 2 | rPhl p 6 mouse anti-rPhl p 6 |
|---|---|---|---|---|---|---|
| patient 1 | 56 | 62 | 48 | 63 | 0 | 5 |
| 2 | 38 | 63 | 38 | 65 | 0 | 29 |
| 3 | 56 | 39 | 53 | 65 | 0 | 18 |
| 4 | 65 | 52 | 54 | 75 | 0 | 9 |
| mean | 54 | 54 | 48 | 67 | 0 | 15 |

B

| with | rPhl p 1 mouse anti-rP5-P1 | rPhl p 5 | rPhl p 1 mouse anti-rPhl p 1 | rPhl p 5 mouse anti-rPhl p 5 |
|---|---|---|---|---|
| patient 1 | 16 | 59 | 33 | 23 |
| 2 | 19 | 67 | 39 | 15 |
| 3 | 14 | 69 | 17 | 40 |
| 4 | 25 | 43 | 29 | 33 |
| mean | 19 | 60 | 30 | 28 |

The invention claimed is:

1. A method of preparing fusion allergens consisting of recombinant polypeptides of two or more different naturally occurring timothy grass pollen allergens for use as immunotherapeutic agents comprising:

(a) providing a polynucleotide sequence encoding the fusion allergen;

(b) introducing said polynucleotide sequence into a host cell;

(c) culturing the host cell obtained in b) under conditions such that the fusion allergen is expressed; and (d) recovering the expressed fusion allergen from the cultured host cell;

(e) testing the fusion allergen as candidate immunotherapeutic agents by administering said allergen to a test animal and selecting as immunotherapeutic agents those fusion allergens that induce IgE-blocking antibodies and induce stronger immune responses compared with the individual components or fragments thereof.

2. The method of claim 1, wherein the polynucleotide sequence encoding the timothy grass pollen allergen is obtained using PCR technology.

3. A pharmaceutical composition comprising one or more fusion allergens of timothy grass pollen allergens as immunotherapeutic agents, wherein said agents consists of recombinant fusion allergens of two or more different naturally occurring timothy grass pollen allergens which have been identified by a method comprising the steps of:

(a) providing fusion allergens of naturally occurring timothy grass pollen allergens;

(b) challenging an immunological model with said fusion allergens;

(c) selecting as candidate immunotherapeutic agents, those fusion allergens which induce IgE-blocking antibodies and induce stronger immune responses compared with the respective allergens which comprise the fusion allergen.

4. A fusion allergen for treatment of IgE-mediated hypersensitivity, wherein said fusion allergen consists of two or more different timothy grass pollen allergens.

5. The fusion allergen of claim 4, wherein said fusion allergen is a fusion protein of two or more different proteins selected from the group consisting of timothy grass pollen allergens rPhl p 1, rPhl p 2, rPhl p 5, and rPhl p 6.

6. The method of claim 1, wherein the recombinant polypeptide of two or more different naturally occurring timothy grass pollen allergens is any selected from the group consisting of rPhl p 5/rPhl p1, rPhl p 2/rPhl p6, rPhl p 6/rPhl p2, and rPhl p 6/rPhl p2/rPhl p 5/rPhl p1.

7. The pharmaceutical composition of claim 3, wherein the recombinant fusion allergens of two or more different naturally occurring timothy is any selected from the group consisting of rPhl p 5/rPhl p1, rPhl p 2/rPhl p6, rPhl p 6/rPhl p2, and rPhl p 6/rPhl p2/rPhl p 5/rPhl p1.

* * * * *

SEQUENCE LISTING

<160> NUMBER OF SEQ ID NOS: 18

<210> SEQ ID NO 1
<211> LENGTH: 27
<212> TYPE: DNA
<213> ORGANISM: artificial sequence
<220> FEATURE:
<223> OTHER INFORMATION: primer

<400> SEQUENCE: 1
ggaattcata tggccgatct cggttac         27

<210> SEQ ID NO 2
<211> LENGTH: 27
<212> TYPE: DNA
<213> ORGANISM: artificial sequence
<220> FEATURE:
<223> OTHER INFORMATION: primer

<400> SEQUENCE: 2
cggggtaccg actttgtagc caccagt         27

```
<210> SEQ ID NO 3
<211> LENGTH: 27
<212> TYPE: DNA
<213> ORGANISM: artificial sequence
<220> FEATURE:
<223> OTHER INFORMATION: primer

<400> SEQUENCE: 3
cggggtacca tgatccccaa ggttccc                                             27

<210> SEQ ID NO 4
<211> LENGTH: 47
<212> TYPE: DNA
<213> ORGANISM: artificial sequence
<220> FEATURE:
<223> OTHER INFORMATION: primer

<400> SEQUENCE: 4
cgggatcctc agtggtggtg gtggtggtgc ttggactcgt agctggt                       47

<210> SEQ ID NO 5
<211> LENGTH: 27
<212> TYPE: DNA
<213> ORGANISM: artificial sequence
<220> FEATURE:
<223> OTHER INFORMATION: primer

<400> SEQUENCE: 5
ggaattcata tggtgccgaa ggtgacg                                             27

<210> SEQ ID NO 6
<211> LENGTH: 39
<212> TYPE: DNA
<213> ORGANISM: artificial sequence
<220> FEATURE:
<223> OTHER INFORMATION: primer

<400> SEQUENCE: 6
cgtggccttc cccataagct tctcttctgg cgcgtaggt                                39

<210> SEQ ID NO 7
<211> LENGTH: 24
<212> TYPE: DNA
<213> ORGANISM: artificial sequence
<220> FEATURE:
<223> OTHER INFORMATION: primer

<400> SEQUENCE: 7
aagcttatgg ggaaggccac gacc                                                24

<210> SEQ ID NO 8
<211> LENGTH: 46
<212> TYPE: DNA
<213> ORGANISM: artificial sequence
<220> FEATURE:
<223> OTHER INFORMATION: primer

<400> SEQUENCE: 8
cgggatccta gtggtggtgg tggtggtgcg cgccgggctt gacagc                        46

<210> SEQ ID NO 9
<211> LENGTH: 27
<212> TYPE: DNA
<213> ORGANISM: artificial sequence
<220> FEATURE:
<223> OTHER INFORMATION: primer
```

```
<400> SEQUENCE: 9
ggaattcata tggtgccgaa ggtgacg                                           27

<210> SEQ ID NO 10
<211> LENGTH: 46
<212> TYPE: DNA
<213> ORGANISM: artificial sequence
<220> FEATURE:
<223> OTHER INFORMATION: primer

<400> SEQUENCE: 10
cgggatccta gtggtggtgg tggtggtgcg cgccgggctt gacagc                      46

<210> SEQ ID NO 11
<211> LENGTH: 30
<212> TYPE: DNA
<213> ORGANISM: artificial sequence
<220> FEATURE:
<223> OTHER INFORMATION: primer

<400> SEQUENCE: 11
ggaattcata tggggaaggc cacgaccgag                                        30

<210> SEQ ID NO 12
<211> LENGTH: 39
<212> TYPE: DNA
<213> ORGANISM: artificial sequence
<220> FEATURE:
<223> OTHER INFORMATION: primer

<400> SEQUENCE: 12
caccttcggc accataagct tcgcgccggg cttgacagc                              39

<210> SEQ ID NO 13
<211> LENGTH: 24
<212> TYPE: DNA
<213> ORGANISM: artificial sequence
<220> FEATURE:
<223> OTHER INFORMATION: primer

<400> SEQUENCE: 13
aagcttatgg tgccgaaggt gacg                                              24

<210> SEQ ID NO 14
<211> LENGTH: 46
<212> TYPE: DNA
<213> ORGANISM: artificial sequence
<220> FEATURE:
<223> OTHER INFORMATION: primer

<400> SEQUENCE: 14
cgggatccta gtggtggtgg tggtggtgct cttctggcgc gtaggt                      46

<210> SEQ ID NO 15
<211> LENGTH: 30
<212> TYPE: DNA
<213> ORGANISM: artificial sequence
<220> FEATURE:
<223> OTHER INFORMATION: primer

<400> SEQUENCE: 15
ggaattcata tggggaaggc cacgaccgag                                        30

<210> SEQ ID NO 16
<211> LENGTH: 46
```

-continued

```
<212> TYPE: DNA
<213> ORGANISM: artificial sequence
<220> FEATURE:
<223> OTHER INFORMATION: primer

<400> SEQUENCE: 16
cgggatccta gtggtggtgg tggtggtgct cttctggcgc gtaggt                    46

<210> SEQ ID NO 17
<211> LENGTH: 30
<212> TYPE: DNA
<213> ORGANISM: artificial sequence
<220> FEATURE:
<223> OTHER INFORMATION: primer

<400> SEQUENCE: 17
ggaattcata tggggaaggc cacgaccgag                                      30

<210> SEQ ID NO 18
<211> LENGTH: 31
<212> TYPE: DNA
<213> ORGANISM: artificial sequence
<220> FEATURE:
<223> OTHER INFORMATION: primer

<400> SEQUENCE: 18
gggatttcca tatgctcttc tggcgcgtag g                                    31
```